(12) United States Patent
Dauwe et al.

(10) Patent No.: US 9,986,403 B2
(45) Date of Patent: May 29, 2018

(54) SYSTEM AND METHOD

(71) Applicant: Amicimi BVBA, Bruges (BE)

(72) Inventors: Stefaan Benedicte Emiel Jacqueline Dauwe, Bruges (BE); Frederic Guy Hélène van Quickenborne, Bruges (BE)

(73) Assignee: Amicimi BVBA, Bruges (BE)

( * ) Notice: Subject to any disclaimer, the term of this patent is extended or adjusted under 35 U.S.C. 154(b) by 0 days. days.

(21) Appl. No.: 15/314,228

(22) PCT Filed: May 21, 2015

(86) PCT No.: PCT/IB2015/053749
§ 371 (c)(1),
(2) Date: Nov. 28, 2016

(87) PCT Pub. No.: WO2015/181689
PCT Pub. Date: Dec. 3, 2015

(65) Prior Publication Data
US 2017/0105105 A1    Apr. 13, 2017

(30) Foreign Application Priority Data
May 26, 2014    (NL) .................................... 2012890

(51) Int. Cl.
*H04M 11/04*    (2006.01)
*H04W 4/22*    (2009.01)
(Continued)

(52) U.S. Cl.
CPC ............ *H04W 4/22* (2013.01); *G08B 25/009* (2013.01); *G08B 25/016* (2013.01); *H04W 76/02* (2013.01)

(58) Field of Classification Search
CPC ...... H04W 4/22; H04W 76/02; G08B 25/009; G08B 25/016
(Continued)

(56) References Cited

U.S. PATENT DOCUMENTS

2004/0266390 A1* 12/2004 Faucher ............. G08B 21/0211
455/404.1
2005/0134455 A1* 6/2005 Binning ................. G08B 7/064
340/539.18
(Continued)

FOREIGN PATENT DOCUMENTS

| WO | 2009036316 A1 | 3/2009 |
| WO | 2013184283 A1 | 12/2013 |

OTHER PUBLICATIONS

Heydon et al., "Battery Service Specification", Bluetooth Specification, Dec. 27, 2011, pp. 1-13, Revision V10r00.
(Continued)

*Primary Examiner* — Khai M Nguyen
(74) *Attorney, Agent, or Firm* — The Webb Law Firm

(57) ABSTRACT

The invention relates to a system provided with —a first apparatus provided with means which can be activated by a cause in order to send a signal to a communication apparatus; and —a communication apparatus provided with •means for receiving the signal; and •means for establishing contact with an emergency response center. The communication apparatus is provided with means which can be activated by reception of the signal and with which the communication apparatus can request data from the first apparatus. The communication apparatus is also provided with assessing means for performing an assessment of the data. The means for establishing contact with the emergency response center can be activated subject to the assessment.

15 Claims, 1 Drawing Sheet

(51) Int. Cl.
  *G08B 25/00*  (2006.01)
  *G08B 25/01*  (2006.01)
  *H04W 76/02*  (2009.01)

(58) Field of Classification Search
  USPC .......................................... 455/404.2, 404.1
  See application file for complete search history.

(56) References Cited

U.S. PATENT DOCUMENTS

| | | |
|---|---|---|
| 2008/0166992 A1 | 7/2008 | Ricordi et al. |
| 2009/0073991 A1 | 3/2009 | Landrum et al. |
| 2010/0315225 A1* | 12/2010 | Teague ................. A61B 5/0024 340/539.12 |
| 2011/0281550 A1 | 11/2011 | Peabody |
| 2012/0003933 A1 | 1/2012 | Baker et al. |
| 2013/0135097 A1* | 5/2013 | Doezema ........... G08B 21/0446 340/539.13 |
| 2013/0331036 A1* | 12/2013 | Baker ................. G06F 19/3418 455/41.3 |
| 2014/0107493 A1 | 4/2014 | Yuen et al. |
| 2014/0273914 A1* | 9/2014 | Mechaley, Jr. ......... H04W 4/22 455/404.1 |

OTHER PUBLICATIONS

Hulvey et al., "Blood Pressure Profile", Bluetooth Profile Specification, Oct. 25, 2011, pp. 1-24, Revision V10r00.

* cited by examiner

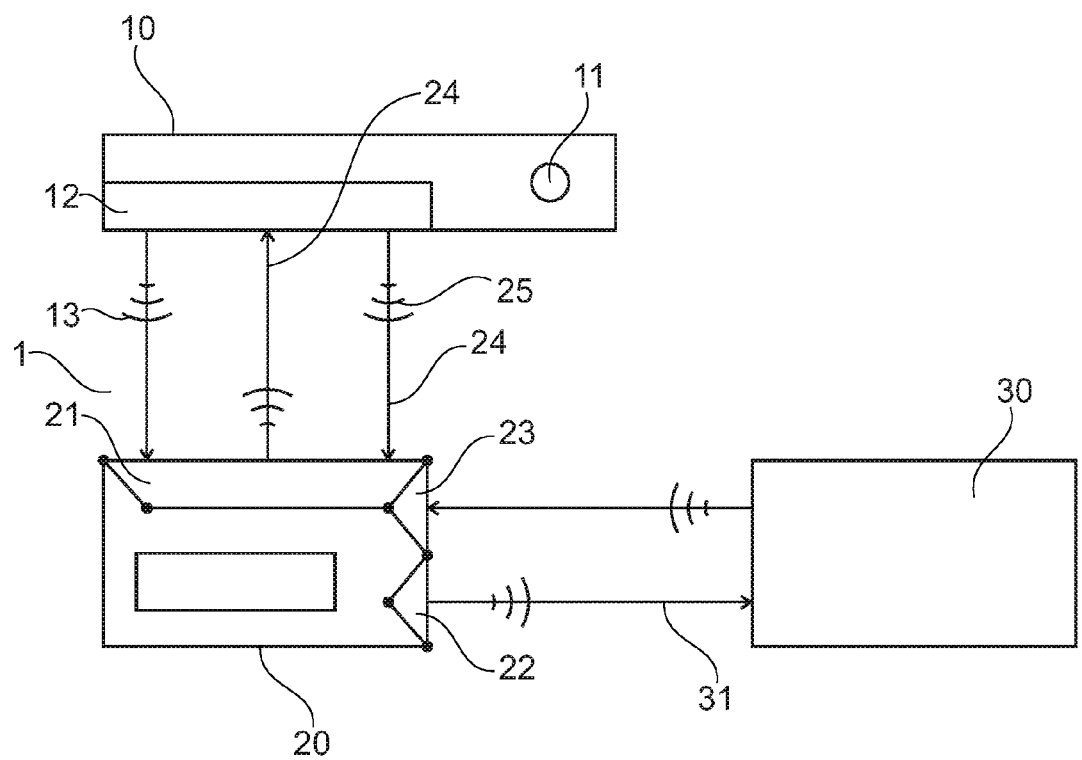

SYSTEM AND METHOD

CROSS-REFERENCE TO RELATED APPLICATIONS

This application is the United States national phase of International Application No. PCT/IB2015/053749 filed May 21, 2015, and claims priority to Dutch Patent Application No. 2012890 filed May 26, 2014, the disclosures of which are hereby incorporated in their entirety by reference.

BACKGROUND OF THE INVENTION

Field of the Invention

The invention relates to a system provided with
a first apparatus provided with means which can be activated by a cause in order to send a signal to a communication apparatus; and
a communication apparatus provided with
means for receiving the signal; and
means for establishing contact with an emergency response centre.
The invention also relates to a method comprising of receiving a signal from a first apparatus with a communication apparatus provided with means for receiving the signal and with means for establishing contact with an emergency response centre.

Description of Related Art

US 20040266390 describes a system in which a telephone calls an operator of an emergency response centre after having received an emergency signal from an emergency device seeking assistance for a carrier of the emergency device. Stored on the emergency device are data which the telephone requests from the emergency device at the request of the operator or automatically and sends on to the operator. The position of the telephone is determined using a GPS receiver in the telephone or through the network to which the telephone is connected. The position is also sent to the operator by the telephone. The operator ensures that the emergency services are not called in unnecessarily. The operator does this on the basis of the data and possible responses from the victim, or the absence of responses.

The data which become available from the emergency device continue to increase, both in type and in the number of data, and the system which has an operator available is not always configured to correctly process the increased amount of data. The system of the operator thus has to automatically identify which data relate to the blood group of the carrier. An increasing amount of data can simultaneously be stored from the medical records of a patient, wherein no standard method of input is available.

People moreover travel frequently and it may occur that the carrier is in an area where contact is made with a centre configured to operate with an emergency device of another type or manufacturer, wherein the technical specifications do not match the technical specifications of the emergency response centre.

At the same time it is advantageous to filter emergency calls in order to prevent emergency services being called in unnecessarily. Speed of response to emergency signals is important and automation assists in a rapid filtering.

The technical problem thus occurs here of being able to automatically filter emergency signals in order to prevent emergency services being called in unnecessarily while the technical specifications of the emergency device also have a large measure of independence from the system of the emergency response centre.

US 2011/0281550 describes a system in which an emergency device automatically sends an emergency signal to a telephone. The telephone then sets up, as emergency call, a voice connection with an emergency response centre of an emergency service and also sends the GPS location of the telephone, unless the emergency device is deactivated quickly enough. The flow of data to the emergency response centre of the emergency service is limited by deactivation. Data about the user, such as information about allergies, are already known at the emergency service and are not transmitted via the telephone and the emergency response centre, this also limiting the flow of data to the emergency response centre of the emergency service at the time of an emergency call. The emergency device can show on a display a notification that a battery voltage is too low. Because the notification is shown on the display, it is not necessary to send this information to the emergency response centre of the emergency service. A display on an emergency device does however make the device heavier and more vulnerable. A display moreover also requires energy, so that the emergency device will more quickly become no longer usable for sending an emergency signal.

The option of deactivating the emergency device does however entail the risk of the emergency device erroneously being deactivated.

Because of the confidentiality of for instance medical data, some people moreover have a standard preference not to store the data at the emergency service. Emergency services moreover have a geographically limited service area and the data must be made known to a number of emergency services if the emergency device is used in different geographical regions.

The technical problem occurs here of being able to automatically filter emergency signals in order to prevent emergency services being called in unnecessarily and also of getting the data to the emergency services in the case of emergency. The technical specifications of the emergency device being largely independent of the system of the emergency response centre is advantageous here.

SUMMARY OF THE INVENTION

It is the object of the invention to provide a system which at least partially solves the problem of the increased amount of data.

The object of the invention is achieved in that a first embodiment of the invention provides a system provided with
a first apparatus provided with means which can be activated by a cause in order to send a signal to a communication apparatus; and
a communication apparatus provided with
means for receiving the signal; and
means for establishing contact with an emergency response centre;
characterized in that the system is provided with:
means which can be activated by reception of the signal and with which the communication apparatus can request data from the first apparatus;
assessing means for performing an assessment of the data; and
in that the means for establishing contact with the emergency response centre can be activated subject to the assessment.

Because the communication apparatus requests data from the first apparatus, the second apparatus can perform an assessment of the data. The means for establishing contact with the emergency response centre can hereby be activated and are thereby dependent on the assessment of the data. Because contact is established subject to the assessment of the data following assessment of the data, the first apparatus can exchange data with the communication apparatus without these being sent to the emergency response centre and there perhaps resulting in confusion or a false alarm.

A second embodiment of the invention is provided by the system of the first embodiment wherein the signal is not dependent on the cause and the data.

Because the signal is not dependent on the cause and the data, there is no necessity to vary the signal, whereby there is more freedom in the design of the system. A larger number of means is thus suitable to function as means which can be activated by the cause and a greater number of means suitable for receiving the signal than if the signal were indeed to be dependent on the cause or on the data.

A third embodiment of the invention is provided by the system of the first or second embodiment wherein the means of the system with which the communication apparatus requests data from the first apparatus comprise means which can be activated by reception of the signal and which set up a connection with the first apparatus over which the data are sent.

Because the communication apparatus sets up a connection with the first apparatus after receiving the signal, it is not necessary to maintain a connection continuously between the first apparatus and the communication apparatus, while this connection is however available to send the data when the signal is received (when a cause has arisen). Bandwidth is hereby saved and the first apparatus and the communication apparatus can operate for longer with the same amount of energy. This is particularly advantageous when the first apparatus and the communication apparatus are powered by batteries, as in the case of the portable devices.

The data are moreover not publicly available because they are sent over the connection. This is certainly an advantage because the data can include medical data of a confidential nature.

In a preferred embodiment the connection is a secure connection over which the data are sent in coded form. The communication apparatus is configured in this embodiment to decode the data. The means for setting up the connection can be configured for this purpose.

A fourth embodiment of the invention is provided by the system of the third embodiment wherein the means which can be activated by a cause send the signal as part of a series of signals, and the means of the system can be activated by any signal of the series of signals in order to set up the connection and request the data.

Because the first apparatus transmits a series of signals, a connection can be set up reliably without the communication apparatus having to listen continuously to incoming signals. The communication apparatus can hereby function with little energy consumption, this being advantageous when the communication apparatus is powered by batteries. The system is moreover more robust in dealing with interference signals than in the case where only one signal is transmitted, since a distorted reception of a signal from the series can be followed by an undistorted reception of a signal from the series.

A fifth embodiment of the invention is provided by the system of the fourth embodiment wherein the communication apparatus can be activated so as to send an instruction to the first apparatus in order to deactivate the means which can activated by the cause.

Without reception of the instruction it is best for high reliability of the follow-up to the causes by the system that the first apparatus continues with transmitting the series of signals: the reception of the instruction serves as confirmation of the follow-up actions.

A connection can thus be set up and the data can be requested by an apparatus which is not able to establish contact with an emergency response centre.

Through deactivation of the means which can be activated by the cause the first apparatus is ready, in the case of a new cause, to transmit this again to the communication apparatus. Energy can moreover hereby be saved, this being very advantageous when the first apparatus is powered by one or more batteries.

In an advantageous embodiment the first apparatus is configured to receive the instruction solely over the connection.

Because the first apparatus can receive the instruction solely over the connection, the system is extra-reliable because it precludes the means which can be activated to send a signal to the communication apparatus being deactivated by an apparatus other than the communication apparatus.

In a preferred embodiment the communication apparatus can be activated to send the instruction by reception of the data.

In another preferred embodiment the communication apparatus can be activated to send the instruction by receiving a call from the emergency response centre.

A sixth embodiment of the invention is provided by the system of the first, second, third, fourth or fifth embodiment wherein the means which can be activated by a cause can be activated by an internal cause.

Because an internal cause can activate the means to send a signal to the communication apparatus, it is possible to maintain the quality or reliability of the first apparatus above a minimum level, for instance with internal quality checks. Too low a quality or reliability need not result here in a call to the emergency response centre.

Because the means for establishing contact with an emergency response centre can be activated subject to the content of the data, less of a load is placed on the emergency response centre while emergency situations are nevertheless reported.

A seventh embodiment of the invention is provided by the system according to any of the foregoing embodiments wherein the communication apparatus comprises notifying means for notifying a user of the communication apparatus that a signal has been received.

Because the communication apparatus notifies the user that it has received the signal, it is not necessary for the first apparatus to notify that the signal has been sent or that the cause has arisen. The first apparatus need not therefore be provided with means for providing such a notification. A notification can consist of a visual notification, for instance a message on the screen of a smart phone, or an audible notification. The first apparatus can hereby comply more easily with set objectives, such as a low weight, watertightness and longer battery operation.

An eighth embodiment of the invention is provided by the system according to the seventh embodiment wherein the notifying means notify the content of one or more of the data.

Notification of the content of one or more data gives the user information about the first apparatus without additional operations being necessary for this purpose and without contact having to be made with the emergency response centre.

The notifying means preferably notify the cause. The user can hereby inspect the cause easily and quickly without notifying means being necessary on the first apparatus for this purpose.

A ninth embodiment of the invention is provided by the system according to any of the foregoing embodiments wherein the data comprise the cause. Because the data comprise the cause, the communication apparatus can perform specific operations which depend on the cause. By processing only the cause the communication apparatus can thus quickly determine whether contact must be made with the emergency response centre. As the skilled person will appreciate, speed is important when notifying an emergency response centre.

The cause can be an internal cause such as a low battery voltage or a panic button being pressed.

If the cause consists of a panic button being pressed on the first apparatus, the way in which the panic button is pressed may signify a difference in cause. The button can for instance be pressed once briefly, twice briefly or pressed and held once, and these three ways can represent different causes.

A tenth embodiment of the invention is provided by the system according to any of the foregoing embodiments wherein the means which can be activated by the reception of the signal and the means for establishing contact with the emergency response centre can be activated by software which can itself be activated on the basis of receiving the signal.

The first apparatus will as often as not use little energy. Because software is activated with a signal, the system is reliable and the communication apparatus is multi-functional. When the communication apparatus receives the signal, the emergency response centre can thus be alerted in the case of emergency if the software for the system has not yet been started up on the communication apparatus by the user. The emergency response centre can also be alerted when the communication apparatus is locked or when the software is running in the background.

It is also an object of the invention to provide a method which at least partially solves the problem of the increased amount of data.

According to another aspect of the invention, an eleventh embodiment of the invention provides a method, comprising of receiving a signal from a first apparatus with a communication apparatus which is provided with means for receiving the signal and with means for establishing contact with an emergency response centre;

characterized by activating, on the basis of reception of the signal, the means with which the communication apparatus requests data from the first apparatus;

performing an assessment of the data with assessing means; and activating the means for establishing contact with the emergency response centre subject to the assessment.

Because the communication apparatus requests data from the first apparatus and then assesses them, the means for establishing contact with the emergency response centre can be activated subject to the assessment of the data. Because contact is established subject to the assessment (and therefore the content) of the data, the first apparatus can exchange data with the communication apparatus without these being sent to the emergency response centre and there perhaps resulting in confusion or a false alarm. The method hereby provides for a good connection of the first apparatus to the emergency response centre and prevents unnecessary contacts with the emergency response centre. Because of the assessment the method can moreover provide diverse functions which the emergency response centre does not support.

A twelfth embodiment of the invention is provided by the method of the eleventh embodiment wherein the step of activating, on the basis of reception of the signal, the means with which the communication apparatus requests data from the first apparatus and the subsequent steps are not dependent on the content of the signal.

Because the steps are not dependent on the content of the signal, there is more design freedom for embodying the method. A larger number of means are thus suitable for receiving the signal than if the signal were dependent on the cause or the data. A larger number of means are also suitable to function in the first apparatus as means which can be activated by a cause, for instance because the signal need not vary depending on the cause or the data.

A thirteenth embodiment of the invention is provided by a method according to the eleventh or the twelfth embodiment wherein means of the communication apparatus are activated by reception of the signal so as to set up a connection with the first apparatus and the data are requested over the connection. Because the communication apparatus sets up a connection with the first apparatus after receiving the signal, it is not necessary to maintain a connection continuously between the first and the communication apparatus, while this connection is however available in order to request the data. Bandwidth is hereby saved and the first apparatus and the communication apparatus can operate for longer with the same amount of energy. This is particularly advantageous when the first apparatus and the communication apparatus are powered by batteries, as in the case of the portable devices.

A fourteenth embodiment of the invention is provided by the method of the thirteenth embodiment wherein the step of activating the means with which the communication apparatus requests data from the first apparatus and the following steps are not dependent on reception of further signals from the first apparatus, reception of each further signal from which is a basis for activating the means with which the communication apparatus requests data from the first apparatus.

The signal and the further signals together form a series of signals. Because the steps are not dependent on reception of further signals, the first apparatus can transmit a series of signals in order to start the method. The data can hereby be requested in reliable manner when the first apparatus transmits a signal without the communication apparatus having to listen continuously to incoming signals. The communication apparatus can hereby make do with little energy, this being advantageous when the communication apparatus is powered by batteries. The possibility of receiving more signals moreover makes the method more robust in dealing with interference signals than in the case where only one signal is received, since a distorted reception of a signal from the series can be followed by an undistorted reception of a signal from the series.

A fifteenth embodiment of the invention is provided by a method according to the fourteenth embodiment wherein the communication apparatus is activated so as to send an instruction to the first apparatus in order to deactivate the means which can be activated by the cause.

Without reception of the instruction it is best for high reliability of the follow-up to the causes by the system that the first apparatus continues with transmitting the series of signals: the first apparatus is after all otherwise unaware of the follow-up actions.

A connection can thus be set up and the data can be requested by an apparatus which is not able to establish contact with an emergency response centre.

Through deactivation of the means which can be activated by the cause the first apparatus is made ready by the communication apparatus, in the case of a new cause, to transmit this again to the communication apparatus. The communication apparatus moreover hereby controls the energy saving on the first apparatus, this being very advantageous when the first apparatus is powered by one or more batteries.

In an advantageous embodiment the first apparatus is configured to receive the instruction solely over the connection.

Because the first apparatus can receive the instruction solely over the connection, the method is extra-reliable because it precludes the means which can be activated to send a signal to the communication apparatus being deactivated by an apparatus other than the communication apparatus.

In a preferred embodiment the communication apparatus is activated to send the instruction by reception of the data.

In another preferred embodiment the communication apparatus is activated to send the instruction by receiving a call from the emergency response centre.

A sixteenth embodiment of the invention is provided by a method according to the eleventh, twelfth, thirteenth, fourteenth or fifteenth embodiment wherein the assessing means can perform the assessment that the signal has been received as a result of an internal cause in the first apparatus.

Because the assessing means can perform the assessment that the signal has been received as a result of an internal cause in the first apparatus, it is possible to maintain the quality or reliability of the first apparatus above a minimum level, for instance with internal quality checks, with a method performed on the communication apparatus. Too low a quality or reliability need not result here in a call to the emergency response centre.

Because the means for establishing contact with an emergency response centre can be activated subject to the assessment of the data, less of a load is placed on the emergency response centre, while emergency situations are nevertheless reported.

A seventeenth embodiment of the invention is provided by a method according to any of the foregoing embodiments wherein the communication apparatus notifies a user that the signal has been received using notifying means.

Because the communication apparatus notifies the user that it has received the signal, it is not necessary for the first apparatus to notify that the signal has been sent or that a cause has arisen. The first apparatus need not therefore be provided with means for providing such a notification. A notification can consist of a visual notification, for instance a message on the screen of a smart phone, or an audible notification. Because the first apparatus does not have to be provided with means for notifying that the signal has been sent or that the cause has arisen, the first apparatus can comply more easily with set objectives, such as a low weight, watertightness and long battery operation.

An eighteenth embodiment of the invention is provided by a method according to the seventeenth embodiment wherein the content of one or more of the data is notified.

Notifying the content of one or more data gives the user information about the first apparatus without additional operations being necessary for this purpose and without contact having to be made with the emergency response centre.

The notifying means preferably notify the cause. The user can hereby inspect the cause easily and quickly without notifying means being necessary on the first apparatus for this purpose.

A nineteenth embodiment of the invention is provided by a method according to any of the foregoing embodiments wherein the data comprise the cause.

Because the data comprise the cause, the communication apparatus can perform specific operations which depend on the cause. By processing only the cause the communication apparatus can thus quickly determine whether contact must be made with the emergency response centre. As the skilled person will appreciate, speed is important when notifying an emergency response centre.

The cause can be an internal cause such as a low battery voltage or a panic button being pressed.

If the cause consists of a panic button being pressed on the first apparatus, the way in which the panic button is pressed may signify a difference in cause. The button can for instance be pressed once briefly, twice briefly or pressed and held once, and these three ways can represent different causes.

A twentieth embodiment of the invention is provided by a method according to any of the foregoing embodiments wherein the means which can be activated by reception of the signal and the means for establishing contact with the emergency response centre are activated by software which is itself activated on the basis of receiving the signal. The first apparatus will as often as not use little energy. Because software is activated with a signal, the method is reliable and the communication apparatus can be used multi-functionally. When the communication apparatus receives the signal, the emergency response centre can thus be alerted in the case of emergency if the software for the system has not yet been started up on the communication apparatus by the user. The emergency response centre can also be alerted when the communication apparatus is locked or when the software is running in the background.

A twenty-first embodiment of the invention is provided by a method according to any of the embodiments eleven to twenty wherein a cause activates means of the first apparatus to send the signal to the communication apparatus.

Because the means for activating the signal are activated on the basis of a cause, the first apparatus can make efficient use of energy.

A twenty-second embodiment of the invention is provided by a computer program comprising means for the purpose, when loaded into a computer, of having the computer perform the method of any of the embodiments 11 to 20.

Examples of embodiments of the invention will be described hereinbelow with reference to the accompanying schematic FIGURE. The schematic FIGURE is not necessarily to scale and some features may be exaggerated for better illustration and explanation of the invention.

Causes for sending a signal to the communication apparatus can be diverse, such as a button being pressed on the first apparatus or for instance measurement of a fall of the first apparatus (wherein the cause can automatically result in the signal being sent), or the measurement of a cardiac arrhythmia, for instance when the first apparatus forms part of a pacemaker.

An internal cause here is a cause which is not dependent on the area surrounding the first apparatus. An example of internal cause is a battery voltage which is too low: the battery voltage does not depend on the surroundings.

An external cause here is a cause which is dependent on the area surrounding the first apparatus. An emergency button being pressed on the first apparatus is an example of an external cause. Because the situation in the surrounding area can cause external triggers, the first apparatus can monitor the surrounding area.

Activation of software is understood here to mean that a processor runs through a part of the code of the software and, as the case arises, the software is loaded into a working memory of the processor. Running the software can take place both in the foreground and in the background.

BRIEF DESCRIPTION OF THE DRAWING

The examples do not otherwise attempt to give an exhaustive list of examples or to otherwise limit the invention to the precise configurations as shown in the FIGURES or described in the following detailed description.

FIG. 1 shows a schematic view of a system according to the invention.

DESCRIPTION OF THE INVENTION

In an example of the invention a system (1) comprises a first apparatus (10) and a communication apparatus (20).

First apparatus (10) is portable and comprises a transceiver (12) provided with an emergency button (11). Transceiver (12) is configured for the use of a wireless connection, in this example via Bluetooth®, in particular Bluetooth Low Energy (BLE). First apparatus (10) is hand-held and fits into a pocket of a pair of trousers. First apparatus (10) is configured to function as an iBeacon™, wherein a series of locating signals is transmitted by transceiver (12). Emergency button (11) operates a switch for the purpose of switching the iBeacon functionality on or off. When the switch is turned on, the iBeacon functionality remains on until it is turned off.

Communication apparatus (20) also comprises a wireless transceiver (21) and is in this case a smart phone on which is installed an app associated with the system (1). Transceiver (21) of smart phone (20) is a Bluetooth transceiver (21) suitable for BLE. The smart phone is also provided with a transceiver (22) for mobile data and a transceiver for GSM (23). Smart phone (20) has a processor and a working memory. The processor can run the app (i.e. a software program) in the working memory, i.e. execute the commands in the code of the app.

The app (a piece of software in the form of a program) has code for the purpose of assessing on the basis of data whether smart phone (20) must establish contact with an emergency response centre (30).

In a first example of the use of the system (1) the app is installed, though not loaded into the working memory, and smart phone (20) is locked.

First apparatus (10) is carried by a person with heart problems. The person carries the first apparatus (10) which in the first instance does not transmit any locating signals.

The person feels at a given moment the necessity to call for assistance and presses emergency button (11) on first apparatus (10). Pressing emergency button (11) causes first apparatus (10) to start transmitting a series of locating signals (13) as beacon by activating means which send the locating signals (13) as beacon.

The locating signals (13) do not depend on the cause or on data about the person. The locating signals are configured for maximum chance of reception by the means of communication apparatus (20) which are configured for this purpose, i.e. the Bluetooth transceiver (21) of communication apparatus (20).

Smart phone (20) receives one of the locating signals (13) with the wireless Bluetooth receiver (21). Smart phone (20) then loads the app into the working memory, after which a start-up routine of the app is run. Smart phone (20) moreover notifies the app that a locating signal (13) has been received.

Because the start-up routine runs after a locating signal has been received, a trigger routine is started by the app following the start-up routine. (This compared to the situation where the app is started manually by a user of smart phone (20), in which case the trigger routine is not started). In the trigger routine the app requests the first apparatus (10) via Bluetooth transceiver (21) to establish a connection via Bluetooth transceiver (21) of smart phone (20) and transceiver (12) of the first apparatus. The app assigns a unique identification number here. After comparison of the unique identification number to identification numbers stored on first apparatus (10) and in the case of recognition the first apparatus (10) assists in establishing the connection with communication apparatus (20).

The app then requests data from first apparatus (10) in the trigger routine over connection (24). First apparatus (10) sends the data (25), such as a unique identification number of first apparatus (10), a notification that emergency button (11) has been pressed and data relating to the person such as gender, height, weight and blood type of the person. The data (25) are also sent over connection (24), so from transceiver (12) of first apparatus (10) to Bluetooth transceiver (21) of communication apparatus (20) which receives the data. First apparatus (10) also sends data (25) from the medical record of the person, such as the name under which the heart problems are known in medical circles. First apparatus (10) also sends the battery voltage of first apparatus (10) as part of the data. These data are also received via Bluetooth transceiver (21) of the communication apparatus.

When it receives the data (25), the communication apparatus, because the processor executes code of the app in the working memory, detects that there is a notification present that emergency button (11) has been pressed. This results in the assessment that there is an emergency and contact must be made with an emergency response centre. The software then activates execution of a routine of the app in order to seek contact with the emergency response centre (30). For this purpose the app sends the data, with the exception of the battery voltage, to an emergency response centre (30) via a mobile internet connection (31). Upon receiving the data the emergency response centre (30) takes action by ringing the smart phone (20) as well as emergency service staff.

Once the emergency response centre (30) has called the smart phone (20), the app sends an instruction via the connection to turn off the locating signal and to break the connection by deactivating the means which send this signal (so transceiver (12) of the first apparatus). This saves the battery of first apparatus (10).

Smart phone (20) has meanwhile also received further locating signals (13) from the series of locating signals (13) but does not respond further to these to the extent these further locating signals (13) were received before the instruction was sent.

In the example the app also requests the location of smart phone (20) before sending the data (25). Smart phone (20) is provided with means for determining the location of smart phone (20) via GPS. The location of smart phone (20) is sent together with the data (25), as is the mobile number of smart phone (20).

In a second example of the use of the system (1) the app is also installed on communication apparatus (20), though in this case the app runs in the background while the user of smart phone (20) plays a game. First apparatus (10) measures that the battery voltage of the battery in first apparatus (10) has fallen below a minimum level. This is cause for first apparatus (10) to begin transmitting a series of locating signals (13).

Smart phone (20) receives a locating signal (13) from the series of locating signals and the app provides a notification that the locating signal (13) has been received. The app then starts the trigger routine. As described above, the app requests first apparatus (10) to establish a connection (24) and then requests data (25) from first apparatus (10), wherein the request for and sending of the data by first apparatus (10) take place over connection (24). Because the data are received by smart phone (20), the data become available to the app. In this second example the data do not comprise the notification that emergency button (11) has been pressed but a notification that the battery voltage of first apparatus (10) is too low. When it receives the data (25), the communication apparatus, because the processor executes code of the app in the working memory, detects that the battery voltage is too low. The app assesses that, because of this internal cause, no contact need be made with an emergency response centre (30) to raise the alarm. It sends an instruction over the Bluetooth connection to break the Bluetooth connection and to switch off Bluetooth receiver (12), whereby transmission of locating signals (13) by first apparatus (10) will cease.

Smart phone (20) has meanwhile received further locating signals (13) from the series of locating signals (13) but does not respond further to these to the extent these further locating signals (13) were received before the instruction was sent.

In addition to sending the instruction, the app moreover ensures that the icon of the app on a display of smart phone (20) is provided with the number "1". The app continues to run in the background the whole time so that the user can continue to play the game and notices nothing of the transmission of the locating signals (13) and the receiving of the locating signals (13), the setting up of the connection (24) and handling of the data (25). As soon as the user stops playing and the app opens in the foreground, the app gives notification that the battery of first apparatus (10) is too low.

Some or all aspects of the invention can be embodied in a computer program product, i.e. in a set of computer program instructions stored on a storage device which is readable by a computer and executable by a computer. The instructions of the present invention can be incorporated into any interpretable or executable code mechanism, including but not limited to scripts, interpretable programs, dynamic link libraries (DLLS) or Java classes. The instructions can form a fully executable program or changes to an existing program or add-ons (plug-ins) for an existing program. Parts of the processing of the present invention can moreover be distributed over different computers or processors for a better performance, reliability or cost.

Storage devices suitable for storing computer program instructions comprise all forms of non-volatile memory, including for instance memory devices based on semiconductors (e.g. EPROM, EEPROM and flash memory), magnetic discs such as internal and external hard discs and removable discs, magneto-optical discs and CD-ROM discs. The computer program products can be distributed on such a storage device or can be offered for download via HTTP, FTP or a similar mechanism, wherein a server is connected to a network such as the internet. Transfer of the computer program product via e-mail is of course also possible.

The invention claimed is:

1. A system comprising:
   a first apparatus provided with a first transceiver which can be activated by an emergency button in order to send a signal to a communication apparatus;
   a communication apparatus provided with a second transceiver for receiving the signal, and a third transceiver for establishing contact with an emergency response centre; and
   an application which can be activated by reception of the signal and with which the communication apparatus can request data from the first apparatus;
   the application performing an assessment of the data; and
   the third transceiver activating the response centre subject to the assessment.

2. The system as claimed in claim 1, wherein the signal is not dependent on the cause and the data.

3. The system as claimed in claim 1, wherein the application can set up a connection with the first apparatus over which the data are sent.

4. The system as claimed in claim 3, wherein the first transceiver sends the signal as part of a series of signals, and the application can be activated by any signal of the series of signals in order to set up the connection and request the data.

5. The system as claimed in claim 4, wherein the communication apparatus can be activated so as to send an instruction to the first apparatus in order to deactivate the signal.

6. The system as claimed in claim 1, wherein the application can be activated by an internal cause of the first apparatus.

7. The system as claimed in claim 1, wherein the communication apparatus comprises notifying means for notifying a user of the communication apparatus that a signal has been received.

8. The system as claimed in claim 7, wherein the notifying means notify the content of one or more of the data.

9. The system as claimed in claim 1, wherein the data comprises notification that emergency button has been pressed.

10. The system as claimed in claim 1, wherein the application and the third transceiver can be activated based on receiving the signal.

11. A method comprising the steps of:
   (a) receiving a signal from a first apparatus with a communication apparatus which is provided with a second transceiver for receiving the signal and with a third transceiver for establishing contact with an emergency response centre;
   (b) activating, on the basis of reception of the signal, the second transceiver with which the communication apparatus requests data from the first apparatus;
   (c) an application performing an assessment of the data; and
   (d) activating the third transceiver to establish contact with the emergency response centre subject to the assessment.

12. The method as claimed in claim 11, wherein steps (b)-(d) are not dependent on the content of the signal.

13. The method as claimed in claim 11, wherein the application is activated by reception of the signal so as to set up a connection with the first apparatus and the data are requested over the connection.

14. The method as claimed in claim 13, wherein the step of activating the application is not dependent on reception of further signals from the first apparatus, reception of each further signal from which is a basis for activating the application.

15. The method as claimed in claim 14, wherein the communication apparatus is activated so as to send an instruction to the first apparatus in order to deactivate a first transceiver which transmits the signal.

\* \* \* \* \*